US00PP27151P2

(12) United States Plant Patent

Hansen et al.

(10) Patent No.: US PP27,151 P2

(45) Date of Patent: Sep. 13, 2016

(54) *HOSTA* PLANT NAMED 'ISLAND BREEZE'

(50) Latin Name: ***Hosta* hybrid (Tratt.)**
Varietal Denomination: Island Breeze

(71) Applicant: Hans A. Hansen, Zeeland, MI (US)

(72) Inventors: Hans A. Hansen, Zeeland, MI (US); Ariel Diaz, Holland, MI (US)

(73) Assignee: Walters Gardens Inc, Zeeland, MI (US)

( * ) Notice: Subject to any disclaimer, the term of this patent is extended or adjusted under 35 U.S.C. 154(b) by 163 days.

(21) Appl. No.: 14/120,060

(22) Filed: Apr. 21, 2014

(51) Int. Cl.
*A01H 5/12* (2006.01)

(52) U.S. Cl.
USPC ..... Plt./353

(58) Field of Classification Search
USPC ..... Plt./353
See application file for complete search history.

(56) References Cited

U.S. PATENT DOCUMENTS

PP20,798 P2 * 3/2010 Fransen ..... Plt./353

OTHER PUBLICATIONS

Pilon. Green Profit. All *Hostas* are not Created Equally. Oct. 29, 2013, pp. 1-2.*
Fransen *Hostas. Hosta* Fruit Punch, retrieved on Sep. 29, 2015, retrieved from the Internet at <https://www.hostaparadise.com/fruit-punch/2062/hosta-details.aspx> pp. 1-2.*
Notes from Hornbaker Gardens Newsletter No. 64, Sep. 2013, retrieved on Jun. 13, 2016, retrieved from the Internet at <http://hornbakergardens.com/image/data/pdf/Newsletters/Hornbaker.64%20web.pdf> 4 pp.*
Susan Martin, Walters Gardens, Inc. Wholesale Catalog, Summer 2013-Spring 2014, Jul. 2013, front cover, and p. 140, Walters Gardens, Inc., Zeeland, Michigan, US.
Walters Gardens Inc. first sales of *Hosta* 'Island Breeze', computer printout from search.

* cited by examiner

*Primary Examiner* — June Hwu

(57) ABSTRACT

A new and distinct *Hosta* plant named 'Island Breeze' with variegated foliage having a wide green margin and bright yellow centers with red stippling at the base of the leaf blades. The broad purple flowers in mid-summer are held attractively above the foliage of the medium-sized plant.

2 Drawing Sheets

LATIN NAME AND VARIETY DENOMINATION OF THE PLANT

Botanical classification: *Hosta* hybrid (Tratt.).
Variety denomination: 'Island Breeze'.

CROSS-REFERENCE TO RELATED PLANTS

*Hosta* 'Island Breeze' differs from its mutation parent, 'Paradise Island' U.S. Plant Pat. No. 20,798, the original mutation parent of 'Paradise Island', 'Fire Island' (not patented), as well as all other *hostas* known to the applicant. *Hosta* 'Fire Island' is a cross between *Hosta longipes f. hypoglauca*×'Crested Surf' (not patented). Other known crosses with *H. longipes f. hypoglauca* include: 'Brandywine' (not patented), 'Chopsticks' (not patented), 'Cinnamon Sticks' (not patented), 'Judy Rocco' (not patented), 'One Man's Treasure' (not patented), 'Red October' (not patented), 'Red Sox' (not patented), 'Valley's Red Raider' (not patented), 'Valley's Roadrunner' (not patented), 'Valley's Sand Dance' (not patented) and 'Valley's White Suit' (not patented). All of the above hybrids of *H. longipes f. hypoglauca* possess some degree of red to purple pigmenting in the petioles, the scape or both. 'Brandywine' has more rounded green leaves than 'Island Breeze'. 'Chopsticks' has more a similar leaf shape to 'Island Breeze', but more green. 'Cinnamon Sticks' is more blue-green and rounded in foliage color and shape compared to the new plant. 'Judy Rocco' is more green to light green in foliage color. The foliage of 'One Man's Treasure' is larger, more rounded and darker green than 'Island Breeze'. 'Red October' has foliage that is more lanceolate and glaucous blue-green than the new plant. 'Red Sox' has more rounded and greener foliage than 'Island Breeze'. 'Valley's Red Raider' is smaller in habit and leaf and more blue-green foliage than 'Island Breeze'. 'Valley's Roadrunner' has more blue-green and flatter foliage than the instant plant. 'Valley's Sand Dance' is smaller with more blue-green in foliage and more glaucous undersides. 'Valley's White Suit' has more densely-glaucous, blue-green, rounded foliage compared to that of 'Island Breeze'. None of the above hybrids are variegated.

Other hybrids with 'Crested Surf' as a parent include: 'Fruit Punch' (not patented) which has solid bright yellow leaves with wavy margins; 'Locomotion' (not patented) with solid blue-green foliage; 'Proud Sentry' (not patented) with creamy-white margined green-centered foliage; and 'Storm' (not patented) which has solid green foliage.

Another similar variegated *hosta* includes 'Red Alert' (not patented) which has similar red stippling in the leaf base but is smaller in habit and foliage with a creamy-yellow margin and light green center. The most similar *hosta* cultivar known to the inventor is the sport parent, 'Paradise Island'. In comparison to 'Paradise Island', 'Island Breeze' has a wider dark-green margin with heavier substance and thicker foliage. The color pattern of the variegation and flower color of 'Paradise Island' and 'Island Breeze' are very similar. 'Island Breeze' is more upright in habit than 'Paradise Island'.

FEDERAL SPONSORSHIP AND FUNDING

This invention was developed without federally sponsored research or development funding.

BACKGROUND OF THE INVENTION

The present invention relates to the new and distinct *hosta* plant, *Hosta* 'Island Breeze' discovered in May of 2010 by Hans A. Hansen and Ariel Diaz at a perennial nursery in Zeeland, Mich., USA as an uninduced whole plant mutation in a tissue cultured crop of *Hosta* 'Paradise Island' U.S. Plant Pat. No. 20,798. The new plant has been successfully asexually propagated both by division and by whole shoot tip tissue culture at a nursery in Zeeland, Mich. and in both asexual propagation systems found to be stable and produce identical plants that maintain the unique characteristics of the original plant.

BRIEF SUMMARY OF THE INVENTION

There are over 5,000 cultivars registered with The American *Hosta* Society, which is the International Cultivar Registration Authority for the genus *Hosta* with an additional similar number of unregistered cultivars. *Hosta* 'Island Breeze' differs from all these registered and unregistered cultivars known to the inventor in the following combined traits:

1. Plant of medium size with upright to slightly arching foliage.
2. Shiny cordate leaves with acute apex and wide dark green margins and bright yellow centers.
3. Variegated leaves have a unique red stippling in the basal portion of blade.
4. Numerous broad flowers of attractively contrasting purple held attractively above foliage in mid-summer.

BRIEF DESCRIPTION OF THE DRAWINGS

The photographs of the three-year old plant demonstrate the overall appearance of the near-mature plant, including the unique traits, grown in a partially shaded garden in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
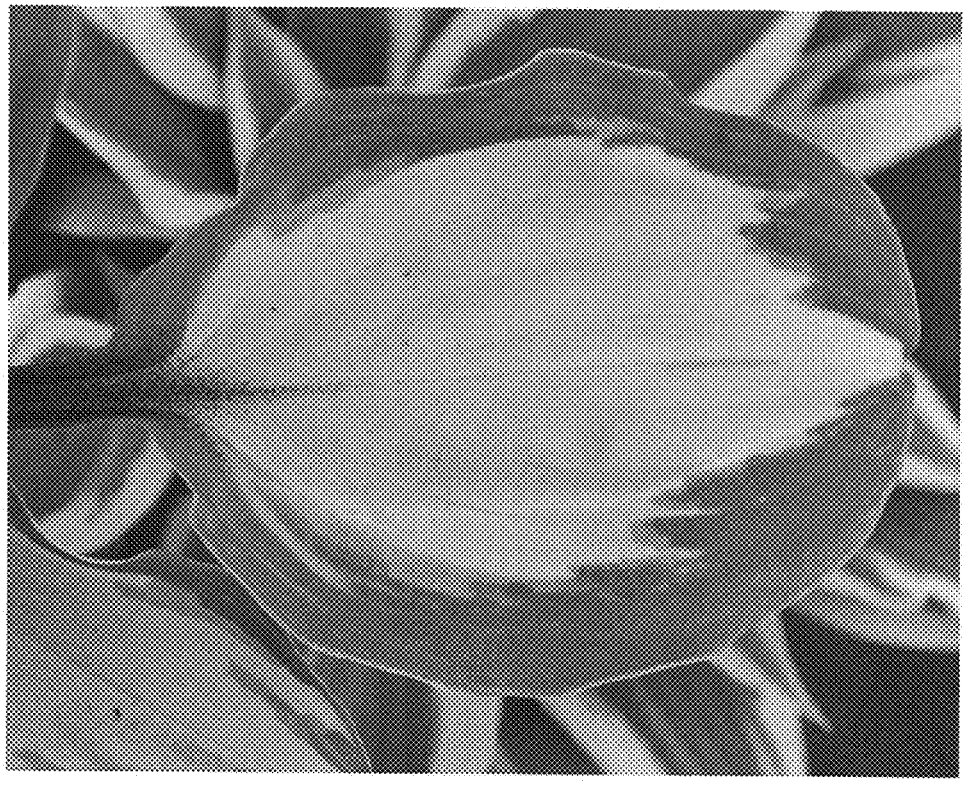
FIG. 1 shows a leaf close-up of a leaf blade showing the variegation and red stippling toward base of leaf blade and in petiole.
Figure 2:
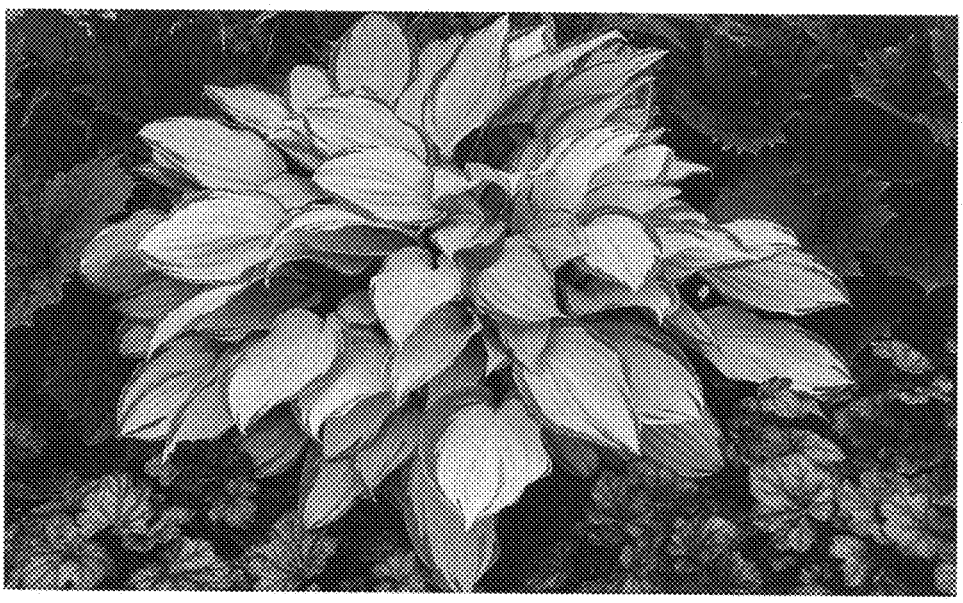
FIG. 2 shows a three-year old plant in a landscape setting about early summer.
Figure 3:
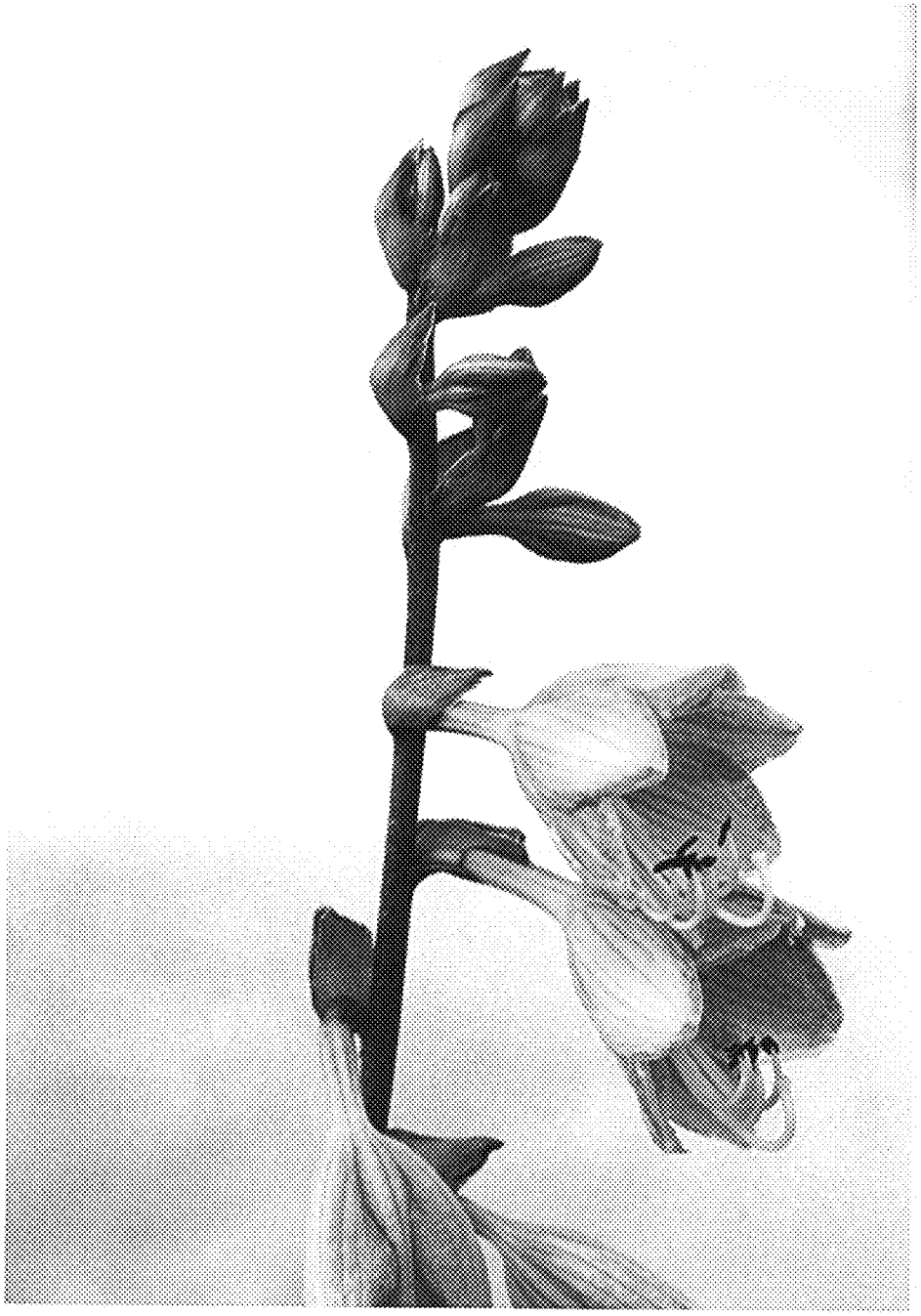
FIG. 3 shows a close-up of the flowers and scape.

The following descriptions and color references are based on the 2001 edition of The Royal Horticultural Society Colour Chart except where common dictionary terms are used. The new plant, *Hosta* 'Island Breeze', has not been observed under all possible environments. The phenotype may vary slightly with different environmental conditions, such as temperature, light, fertility, moisture and specimen maturity, but without any change in the genotype. The following observations and size descriptions are of a three-year old plant in a trial garden in Zeeland, Mich. with 50% artificial shade, supplemental water and light fertilizer.

Botanical classification: *Hosta* hybrid.

Sport parentage: *Hosta* 'Paradise Island'.

Propagation method: By sterile laboratory tissue culture propagation and garden division.

Growth rate: Moderate.

Crop time: Summer growing 10 to 12 weeks to finish in a one-liter container.

Time to initiate roots from tissue culture about two and a half weeks:

Plant description:

*Plant shape and habit*.—Hardy, long-lived, herbaceous perennial, densely rhizomatous, forming a mounded clump in maturity, with basal rosette leaves; usually bilateral and radially symmetrical.

*Roots*.—Normal, fleshy, lightly branching; color cream-colored in normal soil, nearest RHS 155D.

*Plant size*.—Foliage height about 32 cm tall; width of plant at the widest point is approximately 48 cm at the widest point just above soil line.

Foliage description:

*Leaf blade*.—Ovate, rounded leaf base with acute apex; entire margins, flat, mostly bilaterally symmetrical, slightly sinuous or pie-crust margins, with moderately impressed veins; width to length ratio of about 1:1.5; average about 15 cm long and 10 cm wide; 7 to 8 pairs of major parallel veins and one main center vein; glabrous; adaxial (top) surface matte becoming slightly lustrous, abaxial surface (bottom) remaining matte throughout growing season; margin variegation portion increasing with age from 3/16 to nearly 7/16 total leaf width.

*Blade color*.—Early season newly expanding foliage adaxial (top) center more yellow than RHS 154B and slightly more green than RHS 1C, adaxial margin between RHS 143D and RHS 143C, intermediate colors comprising RHS 145A, nearest RHS 144B, and between RHS N144B and RHS 154A in small irregular patches between the margin and center; early season newly expanding abaxial (bottom) center between RHS 151D and RHS 154B, abaxial margin between RHS 138C and RHS 138B, intermediate colors comprising nearest RHS N144D and 145B in very small irregular patches between the margin and center; mid-season and later adaxial center between RHS 1A and RHS 1B, margin between RHS 139B and RHS 141B with small irregular intermediate patches comprising nearest RHS N144D, nearest RHS 151D; mid-season and later abaxial center nearest RHS 154B, margins between RHS 139C and RHS 141B with small irregular intermediate patches comprising nearest RHS N144D and RHS 145B; adaxial and abaxial leaf blade bases contain red stippling concentrated toward base and midrib and going up 1/3 of the way into the leaf nearest RHS N186C.

*Veins*.—7 to 8 pairs of major parallel veins, with one major center vein.

*Vein color*.—Nearly identical to the leaf margin and leaf center of the adaxial and abaxial sides in each respective season of leaf development.

*Petioles*.—Concavo-convex, glabrous, glaucous, upright to arching; about 15 cm long and about 1.0 cm wide measured at 3 cm above soil line.

*Petiole color*.—Adaxial and abaxial margins of petiole between RHS 139B and RHS 141B; adaxial and abaxial center nearest RHS N144D, with high concentration of red stippling nearest RHS N186C along the entire petiole of both surfaces, with the highest concentration of red stippling near the base, becoming almost solid RHS N186C toward base.

Flower description:

*Buds*.—Glabrous, clavate, acute apex with longer thin base; one day prior to opening about 5.0 cm long and 1.7 cm wide at the broadest portion.

*Bud color*.—Three days prior to opening between RHS 90B and RHS 90C at bulb portion; one day prior to opening nearest RHS 92C on the bulb portion; base tube portion of buds three days prior to opening is nearest RHS 90D with slight green tinting of nearest RHS N138D, one day prior to opening the base tube portion of buds is nearest RHS 91B; veins on bulbs one day prior to opening between RHS 92B and RHS 92C; veins on bulbs three days prior to opening nearest RHS 90B.

*Flowers*.—Perfect; single; 24 to 34 per scape; each subtended by bract; funnelform; about 5.2 cm wide and 6.5 cm long, fused in about the proximal 5.0 cm, (distal flowers slightly smaller); remain open for a normal period, usually one to two days on or cut from plant; scapes remain effective from mid-July into mid-August in Zeeland, Mich.

*Flower attitude*.—Nearly horizontal.

*Fragrance*.—None detected.

*Tepals*.—Two identical sets of three fused at the basal two thirds; acute apex; margins entire; glabrous, approximately 6.5 cm long and 1.4 cm wide.

*Tepal color*.—Both sets similarly colored, abaxial tepal color between RHS 92C and RHS 91C; adaxial tepal color nearest RHS 85C.

*Pedicel*.—Cylindrical, slightly curved downward, slightly glaucous, glabrous; about 7 mm long and 3 mm diameter.

*Pedicel color*.—Nearest RHS 138C with slight tinting of nearest RHS 85A.

*Peduncle*.—Cylindrical, glaucous, glabrous, unbranched; usually one per division, vertical to slightly arching to about 75 degrees from horizontal; about 5 mm diameter at base, about 40 cm tall.

*Peduncle color*.—Between RHS N144B and RHS N144C with heavy stippling of between RHS N186C and RHS N186D.

*Bracts*.—Subtending each flower, lanceolate, entire, glaucous, glabrous, concavo-convex, widest at middle and tapering to acute apex, sessile, clasping about ½ peduncle; protruding upward about 20 degree angle away from scape at time of flower opening; with lowest about 1.5 cm long and 0.5 cm wide before first flower, progressively decreasing distally in length; drying as flowers open or shortly thereafter.

*Bract color*.—Adaxial and abaxial between RHS 144A and RHS 143C on the margin and nearest RHS 151D in the center with tinting concentrated at the base and extending distally of between RHS 187C and RHS N186C; drying to nearest RHS 161B.

Gynoecium: Single; tri-carpelled.

*Style*.—About 7.5 cm long, 1 mm diameter, curled upward 90 degrees at distal ¼; color lighter (more white) than RHS 155D the whole length.

*Stigma*.—Rounded, 1 mm to 2 mm in diameter, color lighter than RHS 155D.

*Ovary*.—Oval, about 6 mm long and 3 mm diameter; color nearest RHS 145B.

Androecium: Six.

*Filaments*.—Six, about 1.0 mm in diameter and 6.8 cm long, shorter than gynoecium; with slight curve upward the proximal ⅓; color lighter than RHS 155D throughout.

*Anthers*.—Oblong; dorsifixed, longitudinal; dehiscing along the center longitudinal axis; about 3 mm long and 1 mm wide, color nearest RHS 176A prior to anthesis and nearest RHS N186A after anthesis.

*Pollen*.—Elliptical, less than 0.1 mm long, nearest RHS 21A.

Fruit: Longitudinally dehiscent capsule; about 2.5 cm long and 4.0 mm diameter; color when mature nearest RHS 161C.

Seeds: About 30 per capsule; endospermic; flattened-elliptic wing surrounding embryo situated toward one end of ellipse; about 6.0 mm long and 2.0 mm wide and 1.0 mm thick at embryo; color nearest RHS 202A.

Disease resistance: 'Island Breeze' is less prone to bleaching out of leaves than 'Fire Island'. Other disease or pest resistance beyond that common to *hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *hostas*.

We claim:

1. A new and distinct ornamental *Hosta* plant named 'Island Breeze' as herein described and illustrated, suitable as a potted plant, for the garden landscaping and for cut flower or leaf arrangements.

* * * * *